United States Patent [19]

Haines et al.

[11] Patent Number: 4,783,452

[45] Date of Patent: Nov. 8, 1988

[54] PLATINUM COORDINATION COMPOUNDS

[75] Inventors: Alan H. Haines, Norwich; Christopher Morley, Nottingham, both of United Kingdom

[73] Assignee: Johnson Matthey Public Limited Company, London, England

[21] Appl. No.: 920,541

[22] Filed: Oct. 20, 1986

[30] Foreign Application Priority Data

Oct. 18, 1985 [GB] United Kingdom ............... 8525689

[51] Int. Cl.$^4$ .................. C07F 15/00; A61K 31/555
[52] U.S. Cl. .................................. 514/184; 549/206; 549/450; 549/451; 549/452

[58] Field of Search .................. 549/206; 514/184

[56] References Cited

U.S. PATENT DOCUMENTS 4,466,924 8/1984 Verbeek et al. .
4,500,465 2/1985 Amundsen et al. .

Primary Examiner—Norma S. Milestone
Attorney, Agent, or Firm—Cushman, Darby & Cushman

[57] ABSTRACT

Coordination compounds of platinum(II) with 4,5-bis-(aminomethyl)-1,3-dioxolane, intended for use in the treatment of cancer. The compounds may exist as monomers or as linear or cyclic polymers.

4 Claims, No Drawings

PLATINUM COORDINATION COMPOUNDS

This invention relates to platinum coordination compounds for the treatment of cancer.

Since the initial discovery by Rosenberg that the compound known generically as "cisplatin" (cis-dichlorodiammine-platinum(II)) is an active drug against certain types of cancer, there have been many attempts to provide analogous compounds which are either more active, less toxic and/or have a broader spectrum of activity. Various promising compounds have emerged as a result, although it has remained impossible from studies of structure/activity relationships to predict with any confidence the extent to which a proposed new compound will show anti-tumour activity.

We have now found that compounds of platinum(II) with certain bis(aminomethyl)-dioxolanes show promise as potential anti-cancer agents.

Accordingly, the present invention provides coordination compounds of platinum(II) with a 4,5-bis-(aminomethyl)1,3-dioxolane.

Compounds according to the invention comprise the general formula

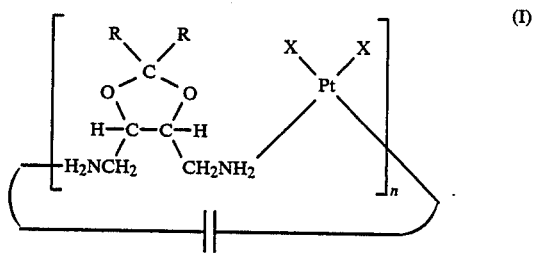

(I)

in which the X groups are the same or different and are selected from mono-valent and di-valent anionic moieties and neutral moieties such that the total charge thereof is -2, or together represent a divalent bidentate moiety, the R groups are the same or different and are selected from H, alkyl and aryl, and n is 1 or an integer greater than 1.

When n is 1, compounds according to the invention have the general formula

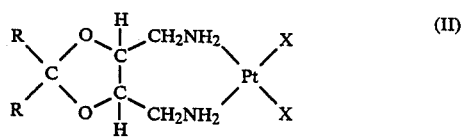

(II)

and when n is greater than 1, compounds according to the invention may be cyclic polymers or linear polymers having the general formula

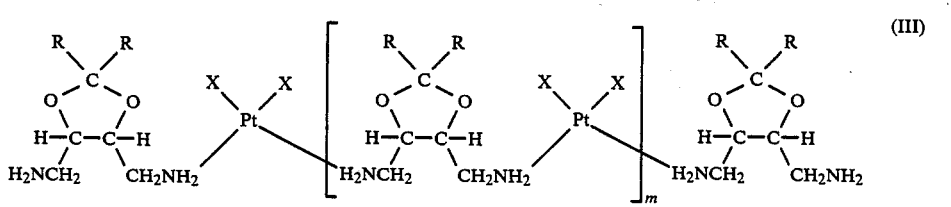

(III)

in which m is zero or an integer up to and including (n−1).

Preferably the X groups in general formula (I), (II) or (III) are both halide, for example chloride. When X is chloride and R is methyl, the monomeric compound (II) may be named cis-dishloro[4,5-bis(aminomethyl-2,2-dimethyl-1,3-dioxolane] platinum (II).

The bis(aminomethyl)-dioxolane moiety of compounds according to the invention can exist in enantiomeric forms (threo stereochemistry) or as a meso-form (erythro stereochemistry) and the invention includes compounds incorporating the individual stereoisomers as well as mixtures thereof.

The enantiomer moieties where the R groups are methyl are as follows, in which the absolute configuration at each chiral centre is designated using the Cahn-Ingold-Prelog nomenclature:

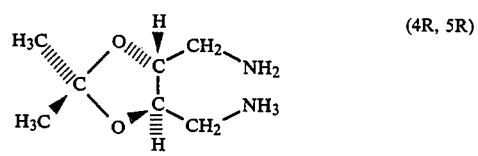

(4R, 5R)

and

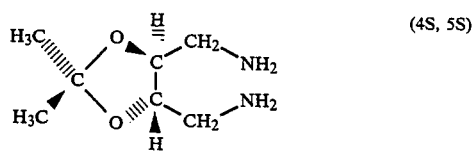

(4S, 5S)

The invention also includes a pharmaceutical composition comprising a compound of general formula (I) in association with a pharmaceutically-acceptable carrier, diluent or excipient.

Compositions according to the invention are suitable for parenteral or oral administration.

Compounds according to the invention may be prepared by double nucleophilic displacement on a di-sulphonate ester of 2,3-O-isopropylidene-threitol (for example the di-methanesulphonate or the di-p-toluenesulphonate) with azide ion to form the diazide, reduction to the corresponding diamine and reaction of the latter with platinum(II).

Such a reaction sequence is illustrated for R=methyl by way of example in Scheme 1, for the preparation of the (4R, 5R)-compound. The starting material, the known 3,4-O-isopropylidene-D-mannitol (1), is reacted with periodate ion, and the product of glycol cleavage is reduced with sodium borohydride to afford 2,3-O-isopropylidene-D-threitol (2). Sulphonylation of (2) with methanesulphonyl chloride affords the di-methanesulphonate (3), which undergoes displacement with azide ion to yield the diazide(4). Catalytic reduction of (4) gives the (4R,5R)-diamine (5), which is reacted, generally without isolation, with potassium tetrachloroplatinate, to afford (4R,5R)-(I).

Scheme 1

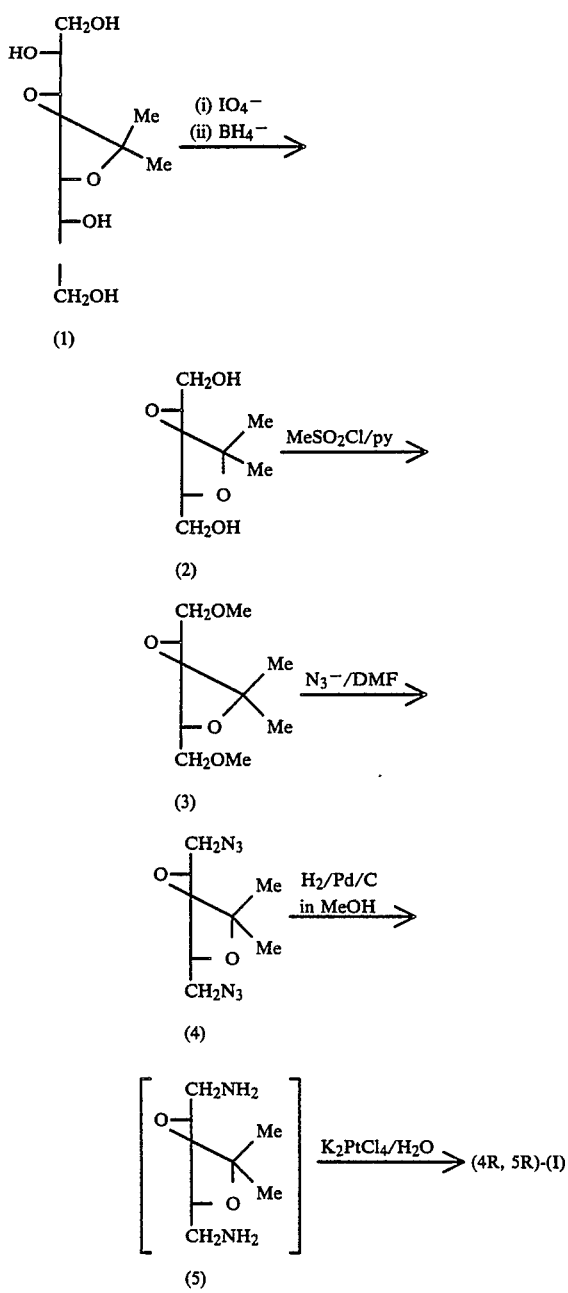

In Scheme 1, the intermediate compound (4), 1,4-diazido-1,4-dideoxy-2,3-O-isopropylidenethreitol (as the D-enantiomer, although the L-enantiomer may be prepared by the same reaction sequence starting from the corresponding L-mannitol), is a novel compound.

Compounds according to the invention where R=methyl may also be prepared by reduction of 2,2-dimethyl-1,3-dioxolane-4, 5-dicarbonitrile to the bis-(aminomethyl)-dioxolane and reaction of the latter with platinum(II). Such a reaction sequence is illustrated by way of example in Scheme 2 for the preparation of the 4S,5S compound. The reaction scheme starts with (2R,3R)-dimethyl 2,3-O-isopropylidenetartrate [(4R,5R)-dimethyl 2,2-dimethyl-1,3-dioxolane-4,5-dicarboxylate] (6) which is converted, by reaction with ammonia, to the dicarboxamide (7), which is dehydrated to give the dicarbonitrile (8). The latter compound is reduced to the (4S,5S)-bis(aminomethyl) compound (9), which is reacted with potassium tetrachloroplatinate to give (4S,5S)-(I). The same reaction sequence, starting with the enantiomer of (6), that is, (2S,3S)-dimethyl 2,3-O-isopropylidenetartrate, could equally be used for the preparation of (4R,5R)-(I).

Scheme 2

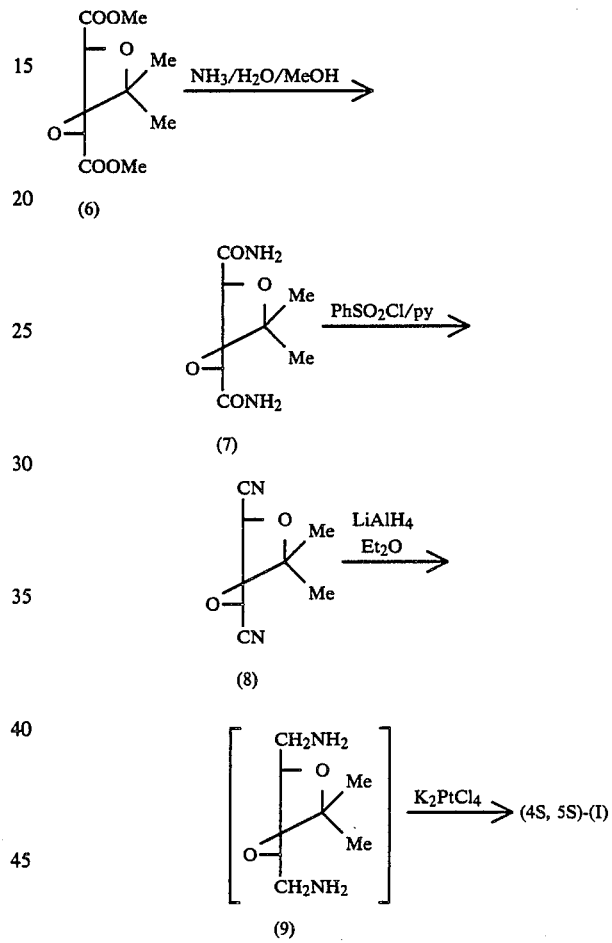

One way of determining whether the compounds as prepared exist according to general formula (I), (II) or (III) may be measurement of the molecular weight.

The steps of the above synthetic reaction schemes will now be described by way of example.

EXAMPLE 1

Preparation of the (4R, 5R)-(I)

The starting material (1) (3,4-O-isopropylidene-D-mannitol) was reacted with sodium periodate and potassium borohydride as described in *J. Chem. Soc., Perkin Trans. I.*, 1972, 275 (the contents of which are herein incorporated by reference) to yield compound (2) in 92% yield. Compound (2) (5.1 g) was dissolved in pyridine (40 ml) and cooled in ice. To this solution was added methanesulphonyl chloride (18 ml), dropwise with stirring. The mixture was allowed to stand at room temperature for 3 hours, after which time it was added to a solution of sodium bicarbonate. This solution was then extracted with dichloromethane (5×50 ml) and the combined extracts were dried (MgSO₄) and concentrated in vacuo. The residue obtained was recrystallised from ethanol to give 2,3-O-isopropylidene-1,4-di-O-methanesulphonyl-D-threitol (3), (6.6 g, 66%), m.p. 83°–85° C.

Compound (3) (3 g) was dissolved in N,N-dimethylformamide (100 ml) and sodium azide (4.9 g) was added. The mixture was heated under reflux for 3 hours. The cooled solution was diluted with dichloromethane (150 ml) and filtered. The solution was then washed with water (2×50 ml), treated with charcoal, dried (MgSO₄) and concentrated in vacuo to give 1,4-diazido-1,4-dideoxy-2,3-O-isopropylidene-D-threitol (4), (1.3 g, 65%).

Compound (4) (1.13 g) was dissolved in "Analar" methanol (50 ml) and hydrogenated over 5% palladium on charcoal (0.2 g) until thin layer chromatography showed that all starting material had been consumed. The suspension was filtered and the filtrate was concentrated in vacuo to give a syrup (0.613 g) whose I.R. spectrum showed no absorption at 2110 cm$^{-1}$ (—N₃) and which was assumed to be (4R,5R)-4,5-bis(aminomethyl)-2,2-dimethyl-1,3-dioxolane (5). This material was dissolved in water (5 ml) and a solution of potassium tetrachloroplatinate (1.58 g) in water (10 ml) was added. The mixture was chilled overnight whereupon a pale orange precipitate appeared. After centrifuging, the supernatant liquor was removed and the precipitate was washed successively with water, ethanol, and diethyl ether. The residue was dried over phosphorus pentoxide to give the product.

The intermediate and final products were characterised by elemental analysis and infra-red spectroscopy.

| | Elemental analysis: | | | |
|---|---|---|---|---|
| | C | H | N | Cl |
| Required: | 19.76 | 3.53 | 6.59 | 16.71 |
| Found: | 19.61 | 3.72 | 6.58 | 16.93 |

EXAMPLE 2

Preparation of (4S, 5S)-(I)

The starting material (6) [(4R,5R-)-dimethyl-2,2-dimethyl-1,3-dioxalane-4,5-dicarboxylate] was reacted in methanol with concentrated aqueous ammonia to give the diamide (7), which was reacted with benzenesulphonyl chloride in dry pyridine to give the dicarbonitrile (8), according to the method disclosed in *J. Chem. Soc., Perkin Trans. I.*, 1985, 795, the contents of which are herein incorporated by reference. The dicarbonitrile (1 g) was dissolved in dry diethyl ether (100 ml) and added to a suspension of lithium aluminium hydride (1.3 g) in dry diethyl ether (40 ml). The suspension was then stirred for 4 hours at room temperature. Water (0.5 ml) was then added to the reaction mixture followed at 5 minute intervals by a 15% sodium hydroxide solution (0.6 ml) and water (1.9 ml). The solution was then filtered and the filtrate was dried (MgSO₄) and concentrated in vacuo to give a syrup which was assumed to be (4S,5S)-4,5-bis(aminomethyl)-2,2-dimethyl-1,3-dioxolane (0.27 g) (9). This syryp was dissolved in water and a solution of potassium tetrachloroplatinate (0.7 g) in water (10 ml) was added with stirring. After 15 minutes. at room temperature a pale orange precipitate began to form. The suspension was stored overnight at 0° C. and, after centrifuging, the supernatant liquor was removed and the precipitate was washed successively with water, ethanol, and diethyl ether. The pale orange powder was then dried over phosphorus pentoxide to give the product.

The intermediate and final products were characterised by elemental analysis and infra-red spectroscopy.

| | Elemental analysis: | | | |
|---|---|---|---|---|
| | C | H | N | Cl |
| Required: | 19.76 | 3.53 | 6.59 | 16.71 |
| Found: | 19.39 | 3.72 | 6.41 | 16.92 |

Compounds according to the invention were screened for anti-tumour activity against ADJ/PC6 tumour implanted into female Balb C⁻ mice, compared with a chemically similar compound not according to the invention. Compounds were administered both parenterally (IP) and orally (PO). Results were as follows:

| COMPOUND | Route | LD₅₀ | ED₉₀ | TI |
|---|---|---|---|---|
| cis-dichloro[(4R,5R)-4,5-bis-(aminomethyl)-2,2-dimethyl-1,3-dioxolane]platinum (II) | IP | 35 | 1.6 | 22.6 |
| | PO | 1100 | 9 | 122 |
| cis-dichloro[(4S,5S)-4,5-bis-(aminomethyl)-2,2-dimethyl-1,3-dioxolane]platinum (II) | IP | 35 | 1.46 | 23.9 |
| | PO | 1130 | 26 | 43.5 |
| cis-dichloro[(4S,5S)-4,5-bis-(aminomethyl)-2-phenyl-1,3-dioxolane]platinum (II) | IP | >800 | 30 | >26 |
| | PO | >1600 | ~1600 | >1 |
| cis-dibromo[4,5-bis(aminomethyl)-2,2-dimethyl-1,3-dioxolane]platinum (II) (racemic mixture) | IP | 21 | 4 | 5.2 |
| cis-dichloro[2,3-dihydroxy-1,2-diamino butane)-platinum (II) (comparative example) | IP | >400 | 380 | >1 |
| | PO | >800 | — | — |

We claim:

1. A compound having the formula

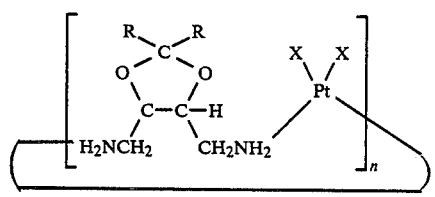

in which the X groups are either both chloride or both bromide, the R groups are either both methyl or one is hydrogen and the other is phenyl, and n is 1.

2. The compound cis-dichloro[(4R,5R)-4,5-bis-(aminomethyl)-2,2-dimethyl-1,3-dioxolane] platinum-(II).

3. The compound cis-dichloro[(4R,5R)-4,5-bis-(aminomethyl)-2,2-dimethyl-1,3-dioxolane] platinum-(II).

4. A composition having anti-tumour activity against implanted ADJ/PC6 comprising a compound according to claim 1 as the active ingredient in association with a pharmaceutically acceptable carrier, diluent or excipient.

* * * * *